(12) United States Patent
Ting et al.

(10) Patent No.: US 11,642,418 B2
(45) Date of Patent: *May 9, 2023

(54) USE OF RADIOLABELED NANOBODY IN PROGNOSIS AND DIAGNOSIS OF CANCER

(71) Applicant: NANOMAB TECHNOLOGY LIMITED, Hong Kong (CN)

(72) Inventors: Hong Hoi Ting, Shanghai (CN); Chung Lim Wong, Shanghai (CN)

(73) Assignee: NANOMAB TECHNOLOGY LIMITED, Hong Kong (HK)

( * ) Notice: Subject to any disclaimer, the term of this patent is extended or adjusted under 35 U.S.C. 154(b) by 373 days.

This patent is subject to a terminal disclaimer.

(21) Appl. No.: 16/647,467

(22) PCT Filed: Sep. 13, 2018

(86) PCT No.: PCT/CN2018/105524
§ 371 (c)(1),
(2) Date: Mar. 13, 2020

(87) PCT Pub. No.: WO2019/052508
PCT Pub. Date: Mar. 21, 2019

(65) Prior Publication Data
US 2020/0276330 A1 Sep. 3, 2020

(30) Foreign Application Priority Data
Sep. 13, 2017 (CN) .......................... 201710822409.5

(51) Int. Cl.
*A61K 47/68* (2017.01)
*A61K 49/16* (2006.01)
*A61K 51/08* (2006.01)
*G01N 33/68* (2006.01)

(52) U.S. Cl.
CPC ...... *A61K 47/6849* (2017.08); *A61K 47/6803* (2017.08); *A61K 49/16* (2013.01); *A61K 51/088* (2013.01); *G01N 33/6872* (2013.01)

(58) Field of Classification Search
CPC ................ A61K 47/00; A61K 47/6849; A61K 47/6803; A61K 49/00; A61K 49/16; A61K 51/00; A61K 51/08; A61K 51/088; A61K 51/1045; A61K 45/00; G01N 33/6872; G01N 33/532; G01N 2333/70596; C07K 16/2827; C07K 2317/22; C07K 2317/569; C07K 2317/76; C07K 2317/92; C07K 2317/56; A61P 35/00
USPC .......... 424/1.11, 1.49, 1.65, 1.69, 1.81, 1.85, 424/1.89, 9.1, 9.2, 9.3, 9.4, 9.6; 514/1, 514/1.1, 19.2, 19.3, 19.4, 19.5, 19.6; 977/773; 530/300
See application file for complete search history.

(56) References Cited

U.S. PATENT DOCUMENTS 10,556,954 B2 * 2/2020 Ting ....................... C12N 15/63

FOREIGN PATENT DOCUMENTS

| CN | 106432501 A | 2/2017 |
|----|----|----|
| WO | 2016197367 A1 | 12/2016 |
| WO | 2017157334 A1 | 9/2017 |

OTHER PUBLICATIONS

International Search Report dated Sep. 13, 2017 corresponding to related International Patent Application No. PCT/CN2018/105524 with English Translation (10 pages).
Written Opinion dated Dec. 6, 2018 corresponding to related International Patent Application No. PCT/CN2018/105524 with English Translation (11 pages).

* cited by examiner

*Primary Examiner* — D. L. Jones
(74) *Attorney, Agent, or Firm* — Polsinelli PC (57) ABSTRACT

Disclosed is the use of a radiolabeled anti-nanobody in the prognosis and diagnosis of cancers. In particular, disclosed is an immunoconjugate for detecting a PD-L1 molecule. The immunoconjugate comprises the VHH chain of a specific anti-PD-L1 nanobody and a radionuclide, and can be used for non-invasive detecting of expression of the object PD-L1 to be detected. The immunoconjugate of the invention has small size and high specificity, and is suitable for systemic detection which simultaneously targets primary and metastatic tumors, and has high accuracy and low radiation dose.

17 Claims, 6 Drawing Sheets
Specification includes a Sequence Listing.

```
SEQ ID NO:1      QVQLQESGGGSVQTGGSLRLSCAASTSIYSNNYMAWFSQAPGKGREGVAAVYIDDGRPYY  60
SEQ ID NO:2      QVQLQESGGGSVQAGGSLRLSCAASGYTYSSDGMGWFRQTPGKEREGVAAISPTGRRTEY  60
SEQ ID NO:3      QVQLQESGGGSVQTGGSLRLSCTASTSIYSNNYMAWFSQSPGKGREGVAAVYMDDGRPYY  60
                 ******:******:*******.**:.***:****** *.**:******:  . ** *

SEQ ID NO:1      ADSVKGRFTISLDSAKNTVYLQMNRLKPEDTAMYYCAAAPGPLSHNYWYTSANYDYWGQG 120
SEQ ID NO:2      ADSVKGRFTISRDNNKNMLSLQMNSLKPEDTGMYYCAREGS---WSFSLANSAVRSWGQG 120
SEQ ID NO:3      ADSVKGRFTISLDSAKNTMYLQMNSLKPEDTAMYYCAAAPGPLSRNYWYTSANYDYWGQG 120
                 ***********.*..**:  ****.*****.*****:      *.: :*..   .****

SEQ ID NO:1      TQVTVSS 127
SEQ ID NO:2      TQVTVSS 124
SEQ ID NO:3      TQVTVSS 127
                 *******
```

FIG. 6

SEQUENCE LISTING

<160> NUMBER OF SEQ ID NOS: 3

<210> SEQ ID NO 1
<211> LENGTH: 127
<212> TYPE: PRT
<213> ORGANISM: Artificial Sequence
<220> FEATURE:
<223> OTHER INFORMATION: VHH chain

<400> SEQUENCE: 1

```
Gln Val Gln Leu Gln Glu Ser Gly Gly Gly Ser Val Gln Thr Gly Gly
1               5                   10                  15

Ser Leu Arg Leu Ser Cys Ala Ala Ser Thr Ser Ile Tyr Ser Asn Asn
            20                  25                  30

Tyr Met Ala Trp Phe Ser Gln Ala Pro Gly Lys Gly Arg Glu Gly Val
        35                  40                  45

Ala Ala Val Tyr Ile Asp Asp Gly Arg Pro Tyr Tyr Ala Asp Ser Val
    50                  55                  60

Lys Gly Arg Phe Thr Ile Ser Leu Asp Ser Ala Lys Asn Thr Val Tyr
65                  70                  75                  80

Leu Gln Met Asn Arg Leu Lys Pro Glu Asp Thr Ala Met Tyr Tyr Cys
                85                  90                  95

Ala Ala Ala Pro Gly Pro Leu Ser His Asn Tyr Trp Tyr Thr Ser Ala
```

```
            100                 105                 110
Asn Tyr Asp Tyr Trp Gly Gln Gly Thr Gln Val Thr Val Ser Ser
        115                 120                 125

<210> SEQ ID NO 2
<211> LENGTH: 124
<212> TYPE: PRT
<213> ORGANISM: Artificial Sequence
<220> FEATURE:
<223> OTHER INFORMATION: VHH chain

<400> SEQUENCE: 2

Gln Val Gln Leu Gln Glu Ser Gly Gly Gly Ser Val Gln Ala Gly Gly
1               5                   10                  15

Ser Leu Arg Leu Ser Cys Ala Ala Ser Gly Tyr Thr Tyr Ser Ser Asp
            20                  25                  30

Gly Met Gly Trp Phe Arg Gln Thr Pro Gly Lys Glu Arg Glu Gly Val
        35                  40                  45

Ala Ala Ile Ser Pro Thr Gly Arg Arg Thr Glu Tyr Ala Asp Ser Val
    50                  55                  60

Lys Gly Arg Phe Thr Ile Ser Arg Asp Asn Lys Asn Met Leu Ser
65                  70                  75                  80

Leu Gln Met Asn Ser Leu Lys Pro Glu Asp Thr Gly Met Tyr Tyr Cys
                85                  90                  95

Ala Arg Glu Gly Ser Trp Ser Phe Ser Leu Ala Asn Ser Ala Val Arg
            100                 105                 110

Ser Trp Gly Gln Gly Thr Gln Val Thr Val Ser Ser
        115                 120

<210> SEQ ID NO 3
<211> LENGTH: 127
<212> TYPE: PRT
<213> ORGANISM: Artificial Sequence
<220> FEATURE:
<223> OTHER INFORMATION: VHH chain

<400> SEQUENCE: 3

Gln Val Gln Leu Gln Glu Ser Gly Gly Gly Ser Val Gln Thr Gly Gly
1               5                   10                  15

Ser Leu Arg Leu Ser Cys Thr Ala Ser Thr Ser Ile Tyr Ser Asn Asn
            20                  25                  30

Tyr Met Ala Trp Phe Ser Gln Ser Pro Gly Lys Gly Arg Glu Gly Val
        35                  40                  45

Ala Ala Val Tyr Met Asp Asp Gly Arg Pro Tyr Ala Asp Ser Val
    50                  55                  60

Lys Gly Arg Phe Thr Ile Ser Leu Asp Ser Ala Lys Asn Thr Met Tyr
65                  70                  75                  80

Leu Gln Met Asn Ser Leu Lys Pro Glu Asp Thr Ala Met Tyr Tyr Cys
                85                  90                  95

Ala Ala Ala Pro Gly Pro Leu Ser Arg Asn Tyr Trp Tyr Thr Ser Ala
            100                 105                 110

Asn Tyr Asp Tyr Trp Gly Gln Gly Thr Gln Val Thr Val Ser Ser
        115                 120                 125
```

USE OF RADIOLABELED NANOBODY IN PROGNOSIS AND DIAGNOSIS OF CANCER

SEQUENCE LISTING

The instant application contains a Sequence Listing which has been submitted electronically in ASCII format and is hereby incorporated by reference in its entirety. Said ASCII copy, created on Mar. 13, 2020, is named 402764_147US_SL_ST25.txt and is 3,854 bytes in size.

TECHNICAL FIELD

The invention relates to the field of biomedical science or bio-imaging, and more particularly to the application of radiolabeled nanobodies for use in prognosis and diagnosis of cancer.

BACKGROUND

PD-1 and its ligand PD-L1 are important targets for tumor immunity. Blocking PD-1/PD-L1 pathways by monoclonal antibodies has received widespread attention in recent years. PD-1 and PD-L1 are immunosuppressive molecules and are important components of the immune system to prevent autoimmune diseases. Activation of the pathway inhibits tumor immune response and induces tumor-specific T cell apoptosis which are closely related to tumor development. PD-1 (CD279) is a type I transmembrane protein that belongs to the immunoglobulin superfamily. It is mainly expressed in activated CD4+ T cells, CD8+ T cells and B cells. PD-L1 (also called B7-H1, CD274) ligand is a member of B7 family. PD-L1 is highly expressed in tumor infiltrating tumor cells (TIC) and diverse malignant tumor cells such as cells in malignant melanoma, non-small cell lung cancer, and head and neck squamous cell carcinoma. PD-1 and PD-L1 monoclonal antibodies showed excellent efficacy and safety in clinical trials. The United States FDA has already approved several anti-PD-1, PD-L1 monoclonal antibodies for the treatment of different cancers including melanoma, non-small cell lung cancer and advanced renal cell carcinoma. There are also multiple clinical trials of PD-1 and PD-L1 monoclonal antibodies in progress.

Upregulated PD-L1 expression in tumor cells prevents the recognition and elimination of tumor cells from immune system. Clinical specimens demonstrate that high expression of PD-L1 in various malignant tumor tissues and TIC shows correlation with poor prognosis in cancer patients. PD-1 and PD-L1 monoclonal antibodies have shown good therapeutic effect in various malignant tumor clinical trials. However, overall response rate is only about 20% where most of the tumor patients with clinical reaction were patients with high expression of PD-L1 in TIC or tumor cells. To screen the patients and improve clinical benefit of treatment, the expression level of PD-L1 in patient should be measured through biopsy prior treatment. Current detection method of PD-L1 expression in patient tissues still depends on tissue puncture IHC. However, because PD-L1 is a dynamic biomarker and the expression level changes with time in the course of treatment, conventional tissue puncture examination method has many limitation in practice. Therefore, it is important to develop more effective diagnostic methods to detect primary and metastatic tumors, using real-time and non-invasive detection and quantitative PD-L1 as a dynamic biomarker, to screen suitable patients for treatment, to monitor the therapeutic effect and to optimize the treatment plan.

Nanobody is currently the smallest antibody molecule, whose binding domain is with a molecular weight of about 1/10 of that of a conventional monoclonal antibody. It was firstly discovered by Belgian scientist Hamers, R in camel blood. It is a very interesting type in engineered antibody products. In addition to antigenic reactivity, nanobody also has some unique functional properties. Nanobody has small molecular weight, strong stability, good solubility, high expression, weak immunogenicity (with more than 70% similarity to human protein sequence), strong penetration, strong targeting, easy humanization, low preparation cost and so on. Small size makes nanobody as an optimal radioisotope targeting carrier. Nanobody quickly penetrates tumor tissue and specifically binds to the target. Unbound nanobody is quickly removed from blood, reducing radiation dose of the body. Compared to conventional antibody, nanobody has more advantages as a tumor tracer.

However, no satisfactory nanobody is currently available for the detection of PD-L1 expression in clinical setting. Therefore, there is an urgent need to develop novel specific nanobodies that are effective against PD-L1.

SUMMARY OF THE INVENTION

The present invention is to provide a class of specific nanobodies effectively targeting PD-L1.

In particular, the present invention is to provide a use of radiolabeled nanobodies effectively targeting PD-L1 for the non-invasive detection of PD-L1 expression in humans.

In a first aspect of the present invention, an immunoconjugate is provided, wherein the immunoconjugate comprises:
  (a) a VHH chain of an anti-PD-L1 nanobody or an anti-PD-L1 nanobody with the VHH chain, wherein the amino acid sequence of the VHH chain is shown as any one of SEQ ID NOS:1-3; and
  (b) a conjugating moiety selected from a group consisting of detectable labels, drugs, toxins, cytokines, radionuclides, enzyme antibodies, antibody Fc fragments, antibody scFv fragments, gold nanoparticles/nanorods, virus particles, liposomes, magnetic nanoparticles, and cells.

In another preferred embodiment, the amino acid sequence of the VHH chain is shown as SEQ ID NO:2.

In another preferred embodiment, the binding of the anti-PD-L1 nanobody to PD-L1 does not interfere the binding of PD-1 to PD-L1.

In another preferred embodiment, the binding region of PD-L1 to the anti-PD-L1 is outside the binding region of PD-L1 to PD-L1.

In another preferred embodiment, the conjugation moiety is a radionuclide.

In another preferred embodiment, the radionuclide comprises:
  (i) a diagnostic radioisotope, which is selected from a group consisting of: Tc-99m, Ga-68, F-18, I-123, I-125, In-111, Ga-67, Cu-64, Zr-89, C-11, and a combination thereof; and/or
  (ii) a therapeutic radioisotope, which is selected from a group consisting of: Lu-177, Y-90, Ac-225, As-211, Bi-212, Bi-213, Cs-137, Cr-51, Co-60, Dy-165, Er-169, Fm-255, Au-198, Ho-166, I-125, I-131, Ir-192, Fe-59, Pb-212, Mo-99, Pd-103, P-32, K-42, Re-186, Re-188, Sm-153, Ru-106, Na24, Sr89, Tb-149, Th-227, Xe-133, Yb-169, Yb-177, and a combination thereof.

In another preferred embodiment, the drug is a cytotoxic drug.

In another preferred embodiment, the cytotoxic drug is selected from a group consisting of: antitubulin drugs, DNA groove binding reagents, DNA replication inhibitors, alkylation reagents, antibiotics, folic acid antagonists, antimetabolites, chemotherapy sensitizers, topoisomerase inhibitors, vinca alkaloids and so on.

Examples of particularly useful cytotoxic drug includes: DNA groove binding reagents, DNA alkylation reagents, and tubulin inhibitors. Typical cytotoxic drugs comprises for example auristatins, camptothecins, doxycycline/duocarmycins, etoposides, maytansines and maytansinoids (compounds such as DM1 and DM4), taxanes, benzodiazepines, or benzodiazepine containing drugs (such as pyrrolo [1,4] benzodiazepine (PBDs), indolinobenzodiazepines, oxazolidinobenzodiazepines, vinca alkaloids, or a combination thereof.

In another preferred embodiment, the toxin is selected from a group consisting of: auristatins (such as auristatin E, auristatin F, MMAE and MMAF), chlortetracycline, methanesol, ricin, A-chain of ricin, cobustine, dokamicin, dorastatin, adriamycin, daunorubicin, paclitaxel, cisplatin, cc1065, ethidium bromide, mitomycin, etoposide, tenoposide, vincristine, vinblastine, colchicine, dihydroxyanthrax diketone, actinomycin, diphtheria toxin, *Pseudomonas* exotoxin (PE) A, PE40, acacia bean toxin, acacia bean toxin A chain, capsule root toxin A chain, α-sarcissus, gelonin, mitogellin, retstrictocin, phenolmycin, enomycin, curicin, croton toxin, calicheamicin, *Sapaonaria officinalis* inhibitor, glucocorticoid, and a combination thereof.

In another preferred embodiment, the immunoconjugate compromises: a multivalent (such as bivalent) VHH chain or anti-PD-L1 nanobody with the VHH chain. The multivalent means that the amino acid sequence of the immunoconjugate contains multiple repeats of the amino acid sequence of the VHH or the anti-PD-L1 nanobody.

In another preferred embodiment, the immunoconjugate is used for the detection of PD-L1 expression in the prognosis and diagnose of cancer.

In another preferred embodiment, the detection is in vivo detection.

In another preferred embodiment, the immunoconjugate is used for treating or preventing tumors with PD-L1 expression (PD-L1 positive).

In a second aspect of the present invention, a PD-L1 detection reagent is provided, which comprises the immunoconjugate of the first aspect of the invention and an acceptable detection carrier.

In another preferred embodiment, the conjugating moiety of the immunoconjugate is a diagnostic radioisotope.

In another preferred embodiment, the acceptable detection carrier is a non-toxic, inert, water-based carrier.

In another preferred embodiment, the detection reagent is selected from a group consisting of: isotope tracers, contrast agents, FACS detection reagents, immunofluorescence detection reagents, magnetic nanoparticles and imaging agents.

In another preferred embodiment, the detection reagent is a contrast agent, and the contrast agent also comprises other preparations for radiography.

In another preferred embodiment, the contrast agent is a contrast agent for MRI (magnetic resonance imaging) or CT (computed tomography).

In another preferred embodiment, the imaging agent comprises two or more signals, such as Ga-68 and Gd, for PET/CT and MRI; or Tc-99m and fluorescent agents, for SPECT/CT and fluorescence detection.

In another preferred embodiment, the detection reagent is for in vivo detection.

In another preferred embodiment, the detection reagent is in the form of liquid or powder (such as water agent, an injection, lyophilized powder, a tablet, a sublingual agent, or an aerosol).

In a third aspect of the present invention, a pharmaceutical composition is provided, which comprises the immunoconjugate in the first aspect of the invention and a pharmaceutical acceptable carrier.

In another preferred embodiment, the conjugate moiety of the immunoconjugate is a drug, toxin, and/or therapeutic radioisotope.

In another preferred embodiment, the pharmaceutical composition further comprises other drugs for the treatment of tumors, such as cytotoxic drugs.

In another preferred embodiment, the pharmaceutical composition is used for treating or preventing tumors with PD-L1 expression (PD-L1 positive).

In another preferred embodiment, the tumors comprise gastric cancer, lymphoma, liver cancer, leukemia, kidney tumor, lung cancer, small intestine cancer, bone cancer, prostate cancer, colorectal cancer, breast cancer, large intestine cancer, prostate cancer, or adrenal tumor.

In another preferred embodiment, the pharmaceutical composition is in the form of injection.

In a fourth aspect of the present invention, a detection kit for PD-L1 expression is provided, which comprises the immunoconjugate in the first aspect of the invention and an instruction manual.

In another preferred embodiment, according to the instruction manual, the kit is for the non-invasive detection of PD-L1 expression in a subject.

In another preferred embodiment, the kit is used for the detection of tumors with PD-L1 expression (PD-L1 positive).

In a fifth aspect of the present invention, the use of the immunoconjugate in the first aspect of the invention is provided for the preparation of (a) a detection reagent, a detection kit or a detection plate for detecting PD-L1 in vivo; (b) pharmaceutical composition for treating or preventing tumors with PD-L1 expression (PD-L1 positive).

In another aspect of the present invention, the use of the immunoconjugate in the first aspect of the invention is provided for the preparation of an imaging agent for detecting PD-L1 expression in vivo.

In a sixth aspect of the present invention, a VHH chain of an anti-PD-L1 nanobody is provided, wherein the amino acid sequence of the VHH chain is shown as any one of SEQ ID NOS:1-3.

In another preferred embodiment, the PD-L1 is a human PD-L1.

Moreover, a VHH chain of an anti-PD-L1 nanobody is provided, wherein the VHH chain comprises a frame region (FR) and a complementary decision region (CDR), wherein the CDR comprises the sequences of any of SEQ ID NOS:1-3 corresponding CDR1, CDR2, and CDR3 as well as FR1, FR2, FR3 and FR4 separated by CDRs 1-3.

Furthermore, a heavy chain variable region of an anti-human PD-L1 antibody is provided, the heavy chain variable region comprises three complementary determining regions CDR1, CDR2, and CDR3 as shown in the SEQ ID NOS:1-3.

In another preferred embodiment, the 3 CDRs include CDR1, CDR2, and CDR3 as shown in Table 2.

In a seventh aspect of the present invention, an anti-PD-L1 nanobody is provided, which targets the PD-L1 epitope and has the VHH chain of amino acid sequence shown in any one of SEQ ID NOS:1-3.

In an eighth aspect of the present invention, a polynucleotide is provided, which encodes a protein selected from a group consisting of: the VHH chain of the anti-PD-L1 nanobody in the sixth aspect of the invention, and the anti-PD-L1 nanobody in the seventh aspect of the invention.

In another preferred embodiment, the Polynucleotides comprises DNA or RNA.

In a ninth aspect of the present invention, an expression vector in provided, which comprises the polynucleotide in the eighth aspect of the invention.

In a tenth aspect of the present invention, a host cell is provided, which contains an expression vector in the ninth aspect of the invention or with the polynucleotide in the eighth aspect of the invention integrated in the genome.

In another preferred embodiment, the host cell is a prokaryote cell or a eukaryotic cell.

In another preferred embodiment, the host cell is selected from a group consisting of: an *E. coli* cell and a yeast cell.

In an eleventh aspect of the present invention, a method for generating an anti-PD-L1 nanobody is provided with steps including:
(a) cultivating the host cell in the tenth aspect of the invention under suitable conditions for producing nanobodies, thereby obtaining cell culture containing the anti-PD-L1 nanobodies; and
(b) separation and recovery of anti-PD-L1 nanobodies from the cell culture.

In another preferred embodiment, the anti-PD-L1 nanobody comprises any one of the amino acid sequences shown in SEQ ID NOS:1-3.

In a twelfth aspect of the present invention, a method of treating diseases is provided, which comprises administering the nanobody and immunoconjugate of the present invention to a subject in need thereof.

In another preferred embodiment, the subject is a mammal, such as human.

Within the scope of the present invention, technical features described above, and technical features described below (such as examples) may be combined with each other to form a new or alternative technical solution. Due to space limitations, they are not repeated here one by one.

BRIEF DESCRIPTION OF THE DRAWINGS

Note: SEQ NO. in the drawing has the same meaning as SEQ ID NO., indicating the sequence numbers in the sequence listing.

DETAILED DESCRIPTION OF THE INVENTION

The present inventors have performed extensive and intensive studies, and unexpectedly discovered an immunoconjugate for the detection of PD-L1 for the first time. The immunoconjugate comprises a VHH chain of a specific anti-PD-L1 nanobody and radionuclides. The binding of the anti-PD-L1 nanobody to PD-L1 does not interfere the binding of PD-1 to PD-L1 and the anti-PD-L1 nanobody can be used for the non-invasive detection of PD-L1 expression in a subject. The immunoconjugate of the invention has a small size and high specificity, and is suitable for the systemic body detection of primary and metastatic tumors with high accuracy and low radiation dose, with high accuracy and low radiation dose. On the basis, the present invention has been completed.

Definitions

As used herein, the terms "nanobody of the present invention", "anti-PD-L1 nanobody of the present invention" and "PD-L1 nanobody of the present invention" are interchangeable and all refer to the nanobodies that specifically recognize and bind to PD-L1 (including human PD-L1). The binding of the anti-PD-L1 nanobody of the present invention to PD-L1 does not interfere the binding of PD-1 to PD-L1. The preferred amino acid sequences of the VHH chain of the specific nanobodies are shown in the SEQ ID NOS:1-3.

The amino acid sequences of the VHH chains of the present invention are shown below, wherein the CDR regions are indicated by underline

```
SEQ ID NO: 1:
QVQLQESGGGSVQTGGSLRLSCAASTSIYSNNYMAWFSQAPGKGREG
VAAVYIDDGRPYYADSVKGRFTISLDSAKNTVYLQMNRLKPEDTAMYYCA
AAPGPLSHNYWYTSANYDYWGQGTQVTVSS

SEQ ID NO: 2:
QVQLQESGGGSVQAGGSLRLSCAASGYTYSSDGMGWFRQTPGKEREGVAA
ISPTGRRTEYADSVKGRFTISRDNNKNMLSLQMNSLKPEDTGMYYCAREG
SWSFSLANSAVRSWGQGTQVTVSS

SEQ ID NO: 3:
QVQLQESGGGSVQTGGSLRLSCTASTSIYSNNYMAWFSQSPGKGREGVAA
VYMDDGRPYYADSVKGRFTISLDSAKNTMYLQMNSLKPEDTAMYYCAAAP
GPLSRNYWYTSANYDYWGQGTQVTVSS
```

Figure 6:
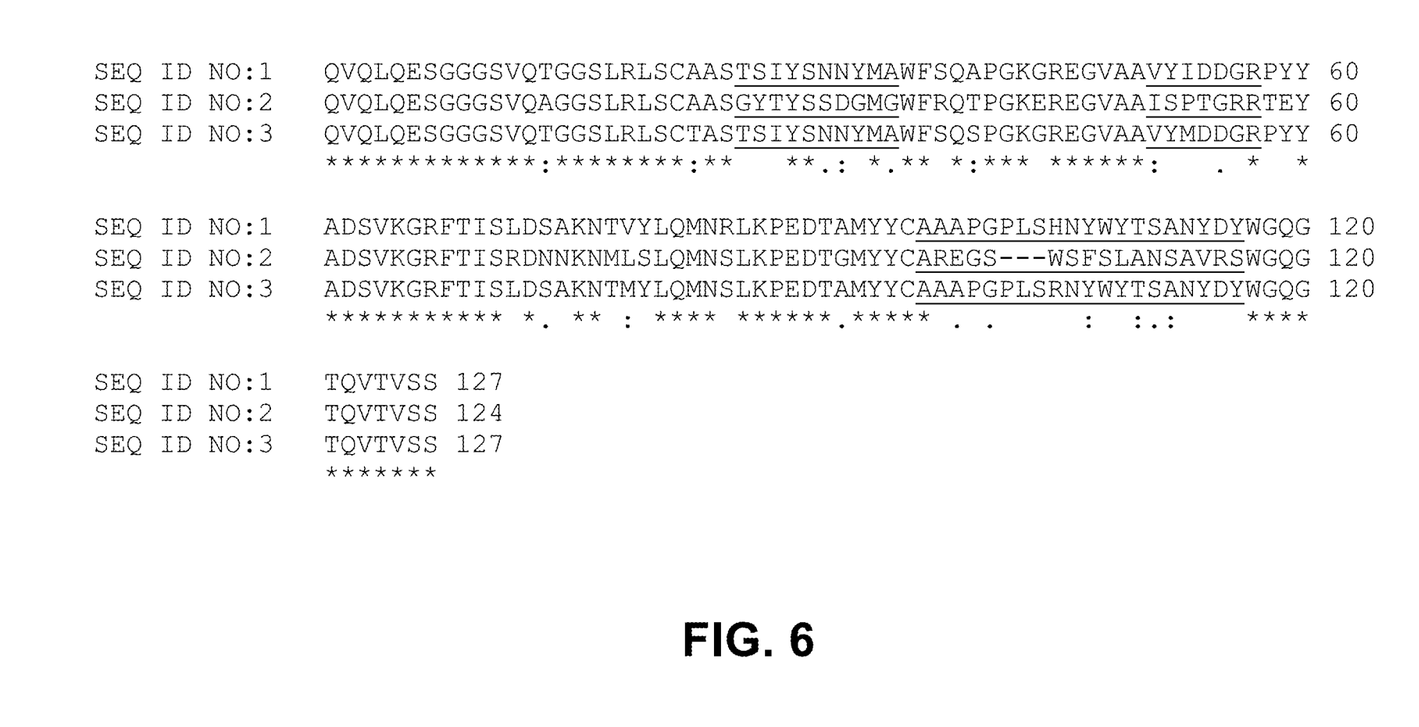
FIG. 6 shows a comparison of the amino acid sequences shown in SEQ ID NOS:1-3, wherein the CDR regions are underlined.

Sequence alignment of the amino acid sequences of the nanobodies of the present invention is shown in FIG. 6. The variance of nanobodies in the present invention is mainly in the CDR region. The nanobody of SEQ ID NO:1 has a sequence identity of >95% compared with the nanobody of SEQ ID NO:3.

As used herein, the term "antibody" or "immunoglobulin" is a heterotetrameric glycosaminoglycan protein of about 150,000 Dalton with the same structural features, consisting of two identical light (L) chains and two identical heavy (H) chains. Each light chain is linked to the heavy chain through a covalent disulfide bond, and the number of disulfide bonds between the heavy chains of different immunoglobulin isoforms is different. Each heavy and light chain also has intra-chain disulfide bonds which are regular spaced. Each heavy chain has a variable region (VH) at one end followed by a plurality of constant regions. Each light chain has a variable region (VL) at one end and a constant region at the other end. The constant region of the light chain is corresponding to the first constant region of the heavy chain, and the variable region of the light chain is corresponding to the variable region of the heavy chain. Special amino acid residues form an interface between the variable regions of the light and heavy chains.

As used herein, the terms "single domain antibody (VHH)" and "nanobody" have the same meaning referring to a variable region of a heavy chain of an cloned antibody, and construct a single domain antibody (VHH) consisting of only one heavy chain variable region. It is the smallest antigen-binding fragment with complete function. Generally, the antibodies with a natural deficiency of the light chain and the heavy chain constant region 1 (CH1) are first obtained, the variable regions of the heavy chain of the antibody are therefore cloned so as to construct a single domain antibody (VHH) consisting of only one heavy chain variable region.

As used herein, the term "variable" refers that certain portions of the variable region in the nanobodies vary in sequences, which forms the binding and specificity of various specific antibodies to their particular antigen. However, variability is not uniformly distributed throughout the nanobody variable region. It is concentrated in three segments called complementarity-determining regions (CDRs) or hypervariable regions in the variable regions of the light and heavy chain. The more conserved part of the variable region is called the framework region (FR). The variable regions of the natural heavy and light chains each contain four FR regions, which are substantially in a n-fold configuration, joined by three CDRs which form a linking loop, and in some cases can form a partially n-fold structure. The CDRs in each chain are closely adjacent to the others by the FR regions and form an antigen-binding site of the antibody with the CDRs of the other chain (see Kabat et al., NIH Publ. No. 91-3242, Volume I, pages 647-669. (1991)). The constant regions are not directly involved in the binding of the antibody to the antigen, but they exhibit different effector functions, for example, involve in antibody-dependent cytotoxicity of the antibodies.

As known by those skilled in the art, immunoconjugates and fusion expression products include: conjugates formed by binding drugs, toxins, cytokines, radionuclides, enzymes, and other diagnostic or therapeutic molecules to the nanobodies or fragments thereof of the present invention. The invention also includes a cell surface label or an antigen that binds to said anti-PD-1 protein nanobody or the fragment thereof.

As used herein, the term "heavy chain variable region" and "VH" can be used interchangeably.

As used herein, the terms "variable region" and "complementary determining region (CDR)" can be used interchangeably.

In another preferred embodiment, the heavy chain variable region of said nanobody comprises 3 complementary determining regions: CDR1, CDR2, and CDR3.

In another preferred embodiment, the heavy chain of said nanobody comprises the above heavy chain variable region and a heavy chain constant region.

According to the present invention, the terms "nanobody of the invention", "protein of the invention", and "polypeptide of the invention" are used interchangeably and all refer to a polypeptide, such as a protein or polypeptide having a heavy chain variable region, that specifically binds to PD-1 protein. They may or may not contain a starting methionine.

The invention also provides other proteins or fusion expression products having the nanobodies of the invention. Specifically, the present invention includes any protein or protein conjugate and fusion expression product (i.e. immunoconjugate and fusion expression product) having a heavy chain containing a variable region, as long as the variable region are identical or at least 90% identical, preferably at least 95% identical to the heavy chain of the nanobody of the present invention.

In general, the antigen-binding properties of a nanobody can be described by three specific regions located in the variable region of the heavy chain, referred as variable regions (CDRs), and the segment is divided into four frame regions (FRs). The amino acid sequences of four FRs are relatively conservative and do not directly participate in binding reactions. These CDRs form a loop structure are spatially close to each other through the β-fold formed by the FRs therebetween. The CDRs on the heavy chain and the CDRs on the corresponding light chain constitute the antigen-binding site of the antibody. The amino acid sequences of the same type of antibodies can be compared to determine which amino acids constitute the FR or CDR regions.

The variable regions of the heavy chains of the antibodies of the invention become a particular interest because at least a part of them is involved in binding antigens. Thus, the present invention includes those molecules having an antibody heavy chain variable region with CDRs, provided that their CDRs are 90% or more (preferably 95% or more, the most preferably 98% or more) identical to the CDRs identified herein.

The present invention includes not only intact antibodies but also fragments of antibody or fusion proteins formed by the antibodies with other sequences, which are immunologically active. Therefore, the present invention also includes fragments, derivatives and analogs of the antibody.

As used herein, the terms "fragment," "derivative," and "analog" refer to a polypeptide that substantially retains the same biological function or activity of an antibody of the invention. Polypeptide fragments, derivatives or analogs of the invention may be (i) polypeptides having one or more conservative or non-conservative amino acid residues (preferably non-conservative amino acid residues) substituted. Such substituted amino acid residues may or may not be encoded by the genetic code; or (ii) a polypeptide having a substituent group in one or more amino acid residues; or (iii) a polypeptide formed by fusing a mature polypeptide and another compound (such as a compound that increases the half-life of the polypeptide, for example, polyethylene glycol); or (iv) a polypeptide formed by fusing an additional amino acid sequence to the polypeptide sequence (e.g., a leader or secretory sequence or a sequence used to purify this polypeptide or a proprotein sequence, or a fusion protein formed with a 6His tag). According to the teachings herein, these fragments, derivatives, and analogs are within the scope of one of ordinary skill in the art.

The antibody of the present invention refers to a polypeptide including the above CDR regions having PD-1 protein binding activity. The term also encompasses variant forms of polypeptides comprising the above CDR regions that have the same function as the antibodies of the invention. These variations include, but are not limited to, deletion, insertion and/or substitution of one or several (usually 1-50, preferably 1-30, more preferably 1-20, optimally 1-10) amino acids, and addition of one or several (generally less than 20, preferably less than 10, and more preferably less than 5) amino acids at C-terminus and/or N-terminus. For example, in the art, the substitution of amino acids with analogical or similar properties usually does not alter the function of the protein. For another example, addition of one or several amino acids at the C-terminus and/or N-terminus usually does not change the function of the protein. The term also includes active fragments and active derivatives of the antibodies of the invention.

The variant forms of the polypeptide include: homologous sequences, conservative variants, allelic variants, natural mutants, induced mutants, proteins encoded by DNAs capable of hybridizing with DNA encoding the antibody of the present invention under high or low stringent conditions, and polypeptides or proteins obtained using antiserum against the antibodies of the invention.

The invention also provides other polypeptides, such as a fusion protein comprising antibodies or fragments thereof. In addition to almost full-length polypeptides, the present invention also includes fragments of the antibodies of the invention. Typically, the fragment has at least about 50 contiguous amino acids of the antibody of the invention, preferably at least about 50 contiguous amino acids, more preferably at least about 80 contiguous amino acids, and most preferably at least about 100 contiguous amino acids.

In the present invention, "a conservative variant of an antibody of the present invention" refers to the polypeptides in which there are up to 10, preferably up to 8, more preferably up to 5, and most preferably up to 3 amino acids substituted by amino acids having analogical or similar properties, compared to the amino acid sequence of the antibody of the present invention. These conservative variant polypeptides are preferably produced according to the amino acid substitutions in Table A.

TABLE A

| Original residue | Representative substitution | Preferable substitution |
|---|---|---|
| Ala (A) | Val; Leu; Ile | Val |
| Arg (R) | Lys; Gln; Asn | Lys |
| Asn (N) | Gln; His; Lys; Arg | Gln |
| Asp (D) | Glu | Glu |
| Cys (C) | Ser | Ser |
| Gln (Q) | Asn | Asn |
| Glu (E) | Asp | Asp |
| Gly (G) | Pro; Ala | Ala |
| His (H) | Asn; Gln; Lys; Arg | Arg |
| Ile (I) | Leu; Val; Met; Ala; Phe | Leu |
| Leu (L) | Ile; Val; Met; Ala; Phe | Ile |
| Lys (K) | Arg; Gln; Asn | Arg |
| Met (M) | Leu; Phe; Ile | Leu |
| Phe (F) | Leu; Val; Ile; Ala; Tyr | Leu |
| Pro (P) | Ala | Ala |
| Ser (S) | Thr | Thr |
| Thr (T) | Ser | Ser |
| Trp (W) | Tyr; Phe | Tyr |

TABLE A-continued

| Original residue | Representative substitution | Preferable substitution |
|---|---|---|
| Tyr (Y) | Trp; Phe; Thr; Ser | Phe |
| Val (V) | Ile; Leu; Met; Phe; Ala | Leu |

The present invention also provides a polynucleotide molecule encoding the above antibody or fragment or fusion protein thereof. Polynucleotides of the invention may be in the form of DNA or RNA. DNA forms include cDNA, genomic DNA, or synthetic DNA. DNA can be single-stranded or double-stranded. DNA can be a coding strand or a non-coding strand.

Polynucleotides encoding the mature polypeptides of the invention include: coding sequences only encoding mature polypeptide; coding sequences for the mature polypeptide and various additional coding sequences; coding sequences (and optional additional coding sequences) and non-coding sequences for the mature polypeptide.

The term "polynucleotide encoding a polypeptide" may include a polynucleotide that encodes the polypeptide, and may also include a polynucleotide that includes additional coding and/or non-coding sequences.

The invention also relates to polynucleotides that hybridize to the sequences described above and that have at least 50%, preferably at least 70%, and more preferably at least 80% identity between the two sequences. The present invention specifically relates to polynucleotides that can be hybridized to the polynucleotides of the present invention under stringent conditions. In the present invention, "stringent conditions" refers to: (1) hybridization and elution at lower ionic strength and higher temperature, such as 0.2× SSC, 0.1% SDS, 60° C.; or (2) additional denaturants during hybridization, such as 50% (v/v) formamide, 0.1% fetal bovine serum/0.1% Ficoll, 42° C., etc.; or (3) hybridization occurs only when the identity between the two sequences is at least over 90%, preferably over 95%. Also, polypeptides encoded by hybridizable polynucleotides have the same biological functions and activities as mature polypeptides.

The full-length nucleotide sequence of the antibody of the present invention or a fragment thereof can generally be obtained by a PCR amplification method, a recombination method, or an artificial synthesis method. One possible method is to synthesize related sequences using synthetic methods, especially when the fragment length is short. In general, a long sequence of fragments can be obtained by first synthesizing a plurality of small fragments and then ligating them. In addition, the coding sequence of the heavy chain and the expression tag (e.g., 6His) can be fused together to form a fusion protein.

Once the concerned sequences are obtained, the sequences of interest can be obtained in large scale using recombinant methods. Usually, sequences can be obtained by cloning it into a vector, transferring it into cells, and then isolating the sequences from the proliferated host cells by conventional methods. Bio-molecules (nucleic acids, proteins, etc.) to which the present invention relates include bio-molecules that exist in isolated form.

At present, DNA sequences encoding the protein of the present invention (or a fragment thereof, or a derivative thereof) can be obtained completely by chemical synthesis. The DNA sequence then can be introduced into various existing DNA molecules (e.g. vectors) and cells known in the art. In addition, mutations can also be introduced into the protein sequences of the invention by chemical synthesis.

The invention also relates to vectors comprising the above-mentioned suitable DNA sequences and suitable promoters or control sequences. These vectors can be used to transform an appropriate host cell so that it can express the protein.

The host cell can be a prokaryotic cell, such as a bacterial cell; or a lower eukaryotic cell, such as a yeast cell; or a higher eukaryotic cell, such as a mammalian cell. Representative examples are: *Escherichia coli, Streptomyces*, bacterial cells such as *Salmonella typhimurium*, fungal cells such as yeast, insect cells of *Drosophila* S2 or Sf9, animal cells of CHO, COS7, 293 cells, and the like.

The transformation of the host cell with the recombinant DNA can be performed using conventional techniques well known to those skilled in the art. When the host is a prokaryotic organism such as *E. coli*, competent cells capable of absorbing DNA can be harvested after the exponential growth phase and treated with the $CaCl_2$ method. The procedures used are well known in the art. Another method is to use $MgCl_2$. If necessary, conversion can also be performed by electroporation. When the host is eukaryotic, the following DNA transfection methods can be used: calcium phosphate coprecipitation, conventional mechanical methods such as microinjection, electroporation, liposome packaging, and the like.

The obtained transformants can be cultured in a conventional manner to express the polypeptide encoded by the gene of the present invention. Depending on the host cells used, the medium used in the culture may be selected from various conventional media. The culture is performed under conditions suitable for the host cells growth. After the host cells are grown to an appropriate cell density, the selected promoter is induced by a suitable method (such as temperature shift or chemical induction) and the cells are incubated for a further period of time.

The recombinant polypeptide in the above method may be expressed intracellularly, or on the cell membrane, or secreted extracellularly. If necessary, the recombinant protein can be isolated and purified by various separation methods by utilizing its physical, chemical and other characteristics. These methods are well-known to those skilled in the art. Examples of these methods include, but are not limited to: conventional renaturation treatment, treatment with a protein precipitation agent (salting out method), centrifugation, osmotic disruption, super treatment, ultra-centrifugation, molecular sieve chromatography (gel filtration), adsorption layer analysis, ion exchange chromatography, high performance liquid chromatography (HPLC), and various other liquid chromatography techniques and the combinations thereof.

The antibodies of the invention may be used alone or in combination or conjugated with a detectable label (for diagnostic purposes), a therapeutic agent, a PK (protein kinase) modification moiety, or any combination thereof.

Detectable labels for diagnostic purposes include, but are not limited to: fluorescent or luminescent markers, radioactive markers, MRI (magnetic resonance imaging) or CT (computed tomography) contrast agents, or enzymes capable of producing detectable products.

Therapeutic agents that can be bound or conjugated to the antibodies of the present invention include, but are not limited to: 1. radionuclides; 2. biological poisons; 3. cytokines such as IL-2, etc.; 4. gold nanoparticles/nanorods; 5. viruses particles; 6. liposome; 7. nano magnetic particles; 8. prodrug activating enzymes (for example, DT-diaphorase (DTD) or biphenyl hydrolase-like protein (BPHL)); 10. chemotherapeutic agents (for example, cisplatin) or any form of nanoparticles, etc.

Immunoconjugate

The present invention also provides an immunoconjugate, comprising:
(a) a VHH chain of an anti-PD-L1 nanobody or an anti-PD-L1 nanobody with the VHH chain, wherein the amino acid sequence of the VHH chain is shown as any one of SEQ ID NOS:1-3; and
(b) a conjugating moiety selected from a group consisting of: radionuclides, enzyme antibodies, cells, and a combinations thereof.

In another preferred embodiment, the conjugating moiety is a radionuclide.

In another preferred embodiment, the conjugating moiety is a drug or toxin.

In another preferred embodiment, the conjugating moiety is a detectable label.

In another preferred embodiment, the conjugation moiety is selected from a group consisting of: fluorescent or luminous labels, radioactive labels, MRI (magnetic resonance imaging) or CT (computed tomography) contrast agents, or enzymes capable of producing detectable products, radionuclides, biotoxins, cytokines (such as IL-2, etc.), antibodies, antibody Fc fragments, antibody scFv fragments, gold nanoparticles/nanorods, viral particles, liposomes, nanoparticles, prodrug activating enzymes (e.g., DT-myocardial xanthase (DTD) or biphenyl hydrolase-like protein (BPHL), chemotherapy agents (such as cisplatin) and any form of nanoparticles.

The immunoconjugate of the present invention can be used for non-invasive detection of PD-L1 expression in a subject. The immunoconjugate has a small size and high specificity, and is suitable for the systemic body detection of primary and metastatic tumors with high accuracy and low radiation dose Kit The present invention also provide a kit comprising the immunoconjugate of the present invention. In a preferred embodiment in the present invention, the kit further comprises a container, an instruction manual, an isotope tracer and one or more reagents selected from the group consisting of: contrast agents, FACS detection reagents, cellular immunofluorescence detection reagents, nanometer magnetic particles and imaging agents.

Preferably, the kit of the present invention is an in vivo diagnostic kit for non-invasive detection of PD-L1 expression in a subject.

Cytotoxic Agent

The conjugating moiety of the immunoconjugate of the present invention comprises: toxins, such as small molecular toxins or enzyme active toxins from bacteria, fungi, plant or animal origin, including the fragments and/or variants thereof. Examples of cytotoxic agents include, but are not limited to: Auristatins (such as Auristatin E, Auristatin F, MMAE and MMAF), chlortetracycline, methanesol, ricin, ricin A-chain, cobustatin, dokamicin, dorastatin, Adriamycin, daunorubicin, paclitaxel, cisplatin, cc1065, ethidium bromide, mitomycin, etoposide, tenoposide, vincristine, vinblastine, colchicine, dihydroxyanthrax diketone, actinomycin, diphtheria toxin, *Pseudomonas* exotoxin (PE) A, PE40, Acacia bean toxin, acacia bean toxin A chain, capsule root toxin A chain, α-sarcissus, gelonin, mitogellin, retstrictocin, phenomycin, enomycin, curicin, croton toxin, calicheamicin, *Sapaonaria officinalis* inhibitors, as well as glucocorticoids and other chemotherapy agents, and radioisotopes such as At211, I131, I125, Y90, Re186, Re188, Sm153, Bi212 or 213, P32 and Lu, including Lu177. Antibodies can also be conjugated to anticancer prodrug activating enzymes that can convert prodrugs into the active forms.

The preferred small molecular drug with high cytotoxicity is selected from the group consisting of monomethylauristatin, galactomycin, medenin, and a combination thereof; more preferably selected from the group consisting of monomethylolastatin-E (MMAE), monomethylolastatin-D (MMAD), monomethylolastatin-F (MMAF), and a combination thereof Pharmaceutical Composition The invention also provides a composition. Preferably, said composition is a pharmaceutical composition comprising the above antibody or active fragment or fusion protein thereof, and a pharmaceutically acceptable carrier. In general, these materials can be formulated in non-toxic, inert, and pharmaceutically acceptable aqueous carrier media wherein the pH is generally about 5-8, preferably about 6-8, although the pH can be varied with the nature of the formulation material and the condition to be treated. The formulated pharmaceutical compositions can be administered by conventional routes including, but not limited to, intratumoral, intraperitoneal, intravenous, or topical administration.

The pharmaceutical composition of the present invention can be directly used to bind PD-1 protein molecule and thus can be used to treat tumors. In addition, other therapeutic agents can also be used at the same time.

The pharmaceutical composition of the present invention contains a safe and effective amount (for example, 0.001-99 wt %, preferably 0.01-90 wt %, and more preferably 0.1-80 wt %) of the above-mentioned antibodies of the present invention (or their conjugates) and pharmaceutically acceptable carriers or excipients. Such carriers include, but are not limited to: saline, buffer, dextrose, water, glycerol, ethanol, and the combinations thereof. The drug formulation should be suitable for the mode of administration. The pharmaceutical composition of the present invention may be prepared in the form of an injection, for example, by a conventional method using physiological saline or an aqueous solution containing glucose and other adjuvant. Pharmaceutical compositions such as injections and solutions are preferably made under aseptic conditions. The amount of active ingredient administered is a therapeutically effective amount, for example, about 10 micrograms/kilogram body weight to about 50 milligrams/kilogram body weight per day. In addition, the polypeptides of the invention can also be used with other therapeutic agents.

When a pharmaceutical composition is used, a safe and effective amount of the immunoconjugate is administered to the mammal, wherein the safe and effective amount is usually at least about 10 micrograms/kilogram body weight, and in most cases, no more than about 50 mg/kilogram body weight, preferably the dose is about 10 micrograms/kilogram body weight to about 10 milligrams/kilogram body weight. Of course, factors such as the route of administration and the patient's health status should be considered to define the specific doses, all of which are within the skills of skilled physicians.

The Main Advantages of Invention Include:
(a) The immunoconjugate of the present invention targets both primary and metastatic tumors simultaneously with whole body imaging for the localization, qualitative and quantitative measurement as well as staging of cancer.
(b) The immunoconjugate of the present invention has small size and high specificity, and can penetrate the tumor tissue more effectively and is more easily excreted by the body, thereby reducing the radiation dose to the non-targeted tissues.
(c) The immunoconjugate of the present invention has a short half-life and a shorter diagnostic time. And the results can quickly be obtained.
(d) The immunoconjugate of the present invention has high specificity, accurate detection and can avoid local false-negative.
(e) The binding of anti-PD-L1 nanobody of the present invention to PD-L1 does not interfere with the binding of the PD-1 to the PD-L1.

The present invention is further illustrated below in conjunction with specific examples. It is to be understood that these examples are not intended to limit the scope of the invention. The experimental methods in the following examples which do not specify the specific conditions are usually in accordance with conventional conditions or conditions recommended by the manufacturer. Unless otherwise stated, percentages and copies are calculated by weight.

EXAMPLES

Example 1. Expression and Purification of the Nanobody in *Escherichia coli*

(1) The corresponding plasmids of nanobodies (sequences of SEQ ID NOS:1-3 as shown in FIG. 6) were electrotransformed into *E. coli* WK6 and coated on LA+ glucose culture plate containing ampicillin and glucose, and incubated overnight at 37° C.

(2) Single colonies were selected and inoculated in 5 mL of LB medium containing ampicillin and incubated overnight in incubator shaker at 37° C.

(3) 1 mL of the overnight inoculated culture was inoculated to 330 mL of TB culture medium and incubated overnight at 37° C. IPTG was added when OD value reached 0.6-1 and the culture was incubated overnight in incubator shaker at 28° C.

(4) Bacteria were collected by centrifugation, and crude extract of antibody was obtained by osmosis method.

(5) The crude extract of antibody was obtained by osmosis method.

(6) The nanobodies with purity >90% were prepared by nickel column ion affinity chromatography.

Nanobodies with the sequences of SEQ ID NOS:1-3 were designated as Nanobody No. 1, Nanobody No. 2, and Nanobody No. 3, respectively.

Figure 1:
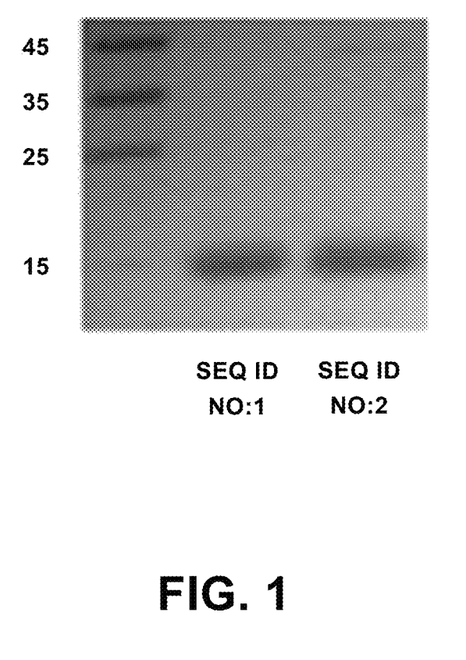
FIG. 1 shows the purification result of anti-PD-L1 nanobodies. M is the protein molecular weight marker, and lane 1-2 correspond to the nanobodies with amino acid sequences of SEQ ID NOS:1-2, respectively.

The purification results were shown in FIG. 1. The purity of nanobody No. 1 and nanobody No. 2 both reached more than 95%.

Example 2. Identification of Nanobody Affinity by Enzyme-Linked Immunosorbent Assay (ELISA)

(1) The PD-L1 was coated on the plate, and IgG and NaHCO$_3$ (100 mM, pH8.2) were used as blank controls. All were incubated overnight at 4° C.

(2) The next day, samples were washed three times with PBST. 1% BSA was added and the plates were sealed at room temperature for 2 hours.

(3) The purified nanobodies were diluted, and reacted with coated PD-L1, IgG and NaHCO$_3$ at room temperature for 1 hour.

(4) Unbound antibodies were washed off with PBST. Mouse anti-HA antibodies were added and the plates were placed at room temperature for 1 hour (5) Unbound antibodies were washed off with PBST. Goat anti-mouse alkaline phosphatase labeled antibodies were then added. Samples were incubated at room temperature for 1 hour.

(6) Unbound antibodies were washed off with PBST and alkaline phosphatase chromogenic solution was added. The absorption value was read at 405 nm via ELISA instrument, and the specificity of the nanobody was judged according to the absorption value.

Figure 2:
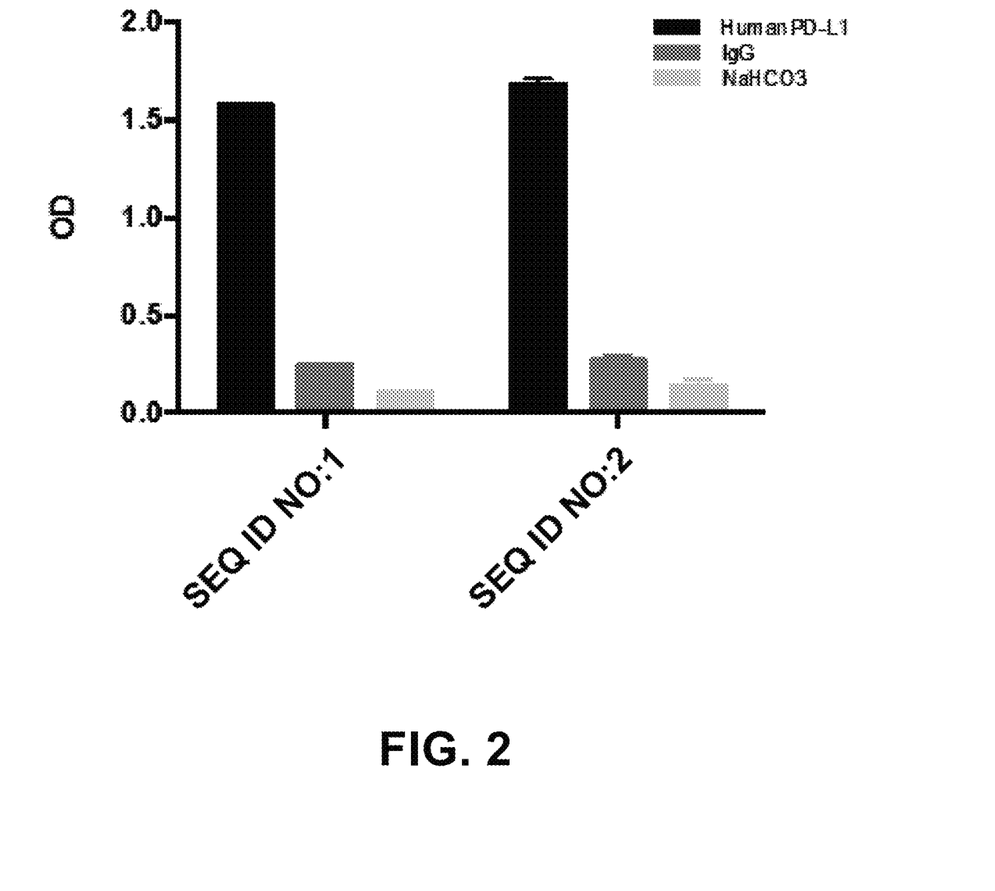
FIG. 2 shows the ELISA results of anti-PD-L1 nanobodies against different antigens. Bar 1-2 correspond to the nanobodies with amino acid sequences of SEQ ID NOS:1-2, respectively.

As shown in FIG. 2, nanobody No. 1 and nanobody No. 2 only bound to PD-L1. The detection result of nanobody No. 3, which was not specifically shown in the figure, was similar to that of nanobody No. 1

The affinity of nanobodies were further determined by gradient dilution.

The results were shown in Table 1. The results showed that the affinity of nanobodies in the present invention reached $1 \times 10^{-9}$ or more.

TABLE 1

Affinity and specificity of the anti-PD-L1 Nanobodies

| Nanobody | kd(nM) | PD-1/PD-L1 Inhibitory effect | HCC827 | A549 |
| --- | --- | --- | --- | --- |
| SEQ ID NO: 1 | 7.96 | 19.3% | 88.10% | 11.53% |
| SEQ ID NO: 2 | 1.62 | 19.3% | 92.80% | 32.60% |
| SEQ ID NO: 3 | 4.46 | 19.2% | 66.55% | 13.50% |
| Positive control | | 2.29% | 92.75% | 61.40% |
| Negative control | | 19.5% | 4.05% | 3.72% |

Example 3. Detection of the Inhibitory Effect of Nanobody in PD-1/PD-L1 Interaction by Flow Cytometry (FACs)

(1) $1 \times 10^6$ HEK293F cells transiently transfected to express human PD-L1 full-length protein were collected and resuspended in 0.5% BSA-PBS buffer. And 10 μg of anti-PD-L1 nanobodies were added, and a positive control, a negative control and blank group (PBS) were set up. All samples were incubated with 5 μg of hPD-1-Fc-Biotin for 20 minutes at 4° C.

(2) The cells were washed twice by PBS and incubated with SA-PE from eBioscience for 20 minutes at 4° C. Cells were washed again with PBS twice and were detected by flow cytometry.

The results were shown in Table 1. The results showed that the nanobodies of present invention did not interfere the binding of PD-1 to PD-L1.

Example 4. Detection of the Specificity of the Nanobody by Flow Cytometry (1) Cell types: HCC827 and A549. Cells were washed twice with PBS.

(2) The Nanobody solution was diluted with PBS. Positive control, negative control and blank group (PBS) were set up at the same time.

(3) Cells were divided into 96-well plates, wherein the number of cells per sample was $3 \times 10^5$. The diluted nanobodies were then added to each well, mixed and placed at 4° C. for 20 min.

(4) Cells were washed twice with PBS and incubated with anti-HA Alexa Fluor 488 for 20 minutes at 4° C.

(5) Cells were washed again twice and detected by BD FACS Calibur.

The results were shown in Table 1. The positive rate of the nanobodies was 67-93% in cell lines with high PD-L1 expression (HCC827) and was 12-33% in cell lines with low PD-L1 expression (A549). The difference between the two cell lines were more than 2 folds, which further suggested that the nanobodies of the present invention were highly specific to PD-L1.

Example 5. 1-125 Labeling, Purification and SPECT Scanning of the Nanobody (1) 150 μL of the nanobody solution was added with 100 μL of 0.02 mol/L pH7.4 phosphate buffer solution and 50 μL, of Na125I solution, and 20 μL of 5 mg/mL chloramine T solution was added to the mixer, and reacted in the mixer for 70 s at room temperature. 200 μL sodium sulfite solution (5 mg/mL) was then added and incubated for 5 minutes.

(2) The nanobodies were separated by PD10 column and eluted using 0.02 mol/L pH7.4 phosphate buffer solution. 10 drops were collected per tube. The radiopurity of I-125 labeled nanobodies was identified by paper chromatography.

(3) $5 \times 10^5$ HCC827 cells with high PD-L1 expression were inoculated in the right armpit of nude mice and the tumor was grown to the size of 150-200 mm³ for the study.

(4) Tumor-bearing mice were anesthetized with isoflurane and were injected through tail vein with I-125 labeled nanobodies (~50 ug, 5 MBq).

(5) Scanning was performed 0.5 hr after administration, and the data was collected with static 15 min SPECT and medium resolution whole body CT.

Figure 3:
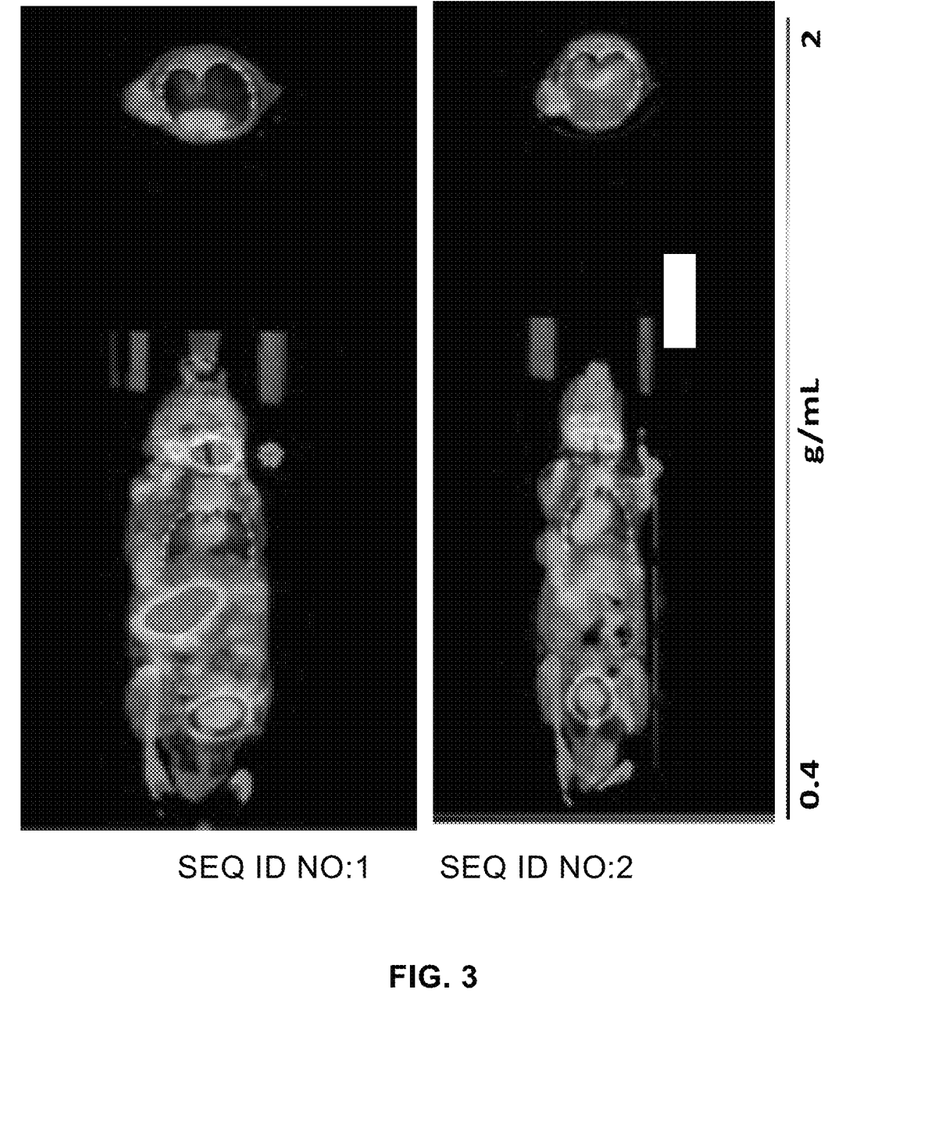
FIG. 3 shows the SPECT-CT imaging result of 1-125 labeled anti-PD-L1 nanobodies in tumor-bearing mice with high PD-L1 expression. Nanobodies with amino acid sequences of SEQ ID NOS:1-2 can effectively accumulate in tumors with high PD-L1 expression, and non-binding antibodies can be quickly cleared from the blood through kidney and bladder.

FIG. 3 and Table 2 show the 30 minute SPECT scan pictures and the bio-distribution data of tumor-bearing mice. The results showed that nanobody No. 1 and nanobody No. 2 can effectively accumulate in the tumor with high PD-L1 expression for the non-invasive detection of PD-L1 expression, thus can be used for the prognosis and diagnosis of cancer. Meanwhile, non-binding antibodies were quickly removed from the blood stream through the kidneys and bladders, reducing the radiation dose of the body and shortening the waiting time for imaging. The imaging result of nanobody No. 3, which was not specifically shown in the figure, was similar to that of nanobody No. 1.

TABLE 2

Bio-distribution of anti-PD-L1 nanobody labeled with I-125 in tumor-bearing mice with high PD-L1 expression

| Name | ID %/g | |
| --- | --- | --- |
| Organ | SEQ ID NO: 1 | SEQ ID NO: 2 |
| Heart | 4.56 ± 0.96 | 4.03 ± 0.18 |
| Lung | 2.96 ± 0.56 | 2.73 ± 0.64 |
| Liver | 4.40 ± 1.25 | 3.08 ± 0.04 |
| Kidney | 20.40 ± 3.30 | 23.63 ± 3.13 |
| Bladder | 117.81 ± 20.61 | 62.35 ± 3.55 |
| Muscle | 1.89 ± 0.31 | 1.25 ± 0.10 |
| Tumor | 3.51 ± 0.44 | 3.27 ± 0.08 |
| Tumor/Heart | 0.78 ± 0.07 | 0.82 ± 0.06 |
| Tumor/Muscle | 1.87 ± 0.08 | 2.64 ± 0.05 |

Example 6. 99mTc Labeling, Separation and Purification of Nanobody, Serum Stability Test and SPECT Imaging Scanning (1) 5.5 mg of $Na_2CO_3$, 15.2 mg of potassium sodium tartrate and 20.5 mg of $NaBH_4$ were added into a 10 mL sterile bottle. CO was passed over for 20 min. And 1 mL of (35mCi) Na [99mTcO$_4$] was added. The bottle was sealed and was left to react for 30 min at 80° C.

(2) 50 μL of the antibody solution was added to 500 μL of 99mTc $(CO)_3(H_2O)_3$ reaction solution (6.56mCi), to react for 90 min at 45-50° C.

(3) The 99mTc labeled nanobodies were separated by PD10 column and eluted with 0.02 mol/L pH7.4 phosphate buffer solution. The radiochemical purity was identified by thin layer chromatography (TLC).

(4) 100 μL of the 99mTc labeled nanobodies were added to 500 μL of mouse or human serum and incubated for 30, 90 and 180 min at 37° C.

(5) The 99mTc labeled nanobody solution was analyzed by SEC HPLC.

Figure 4:
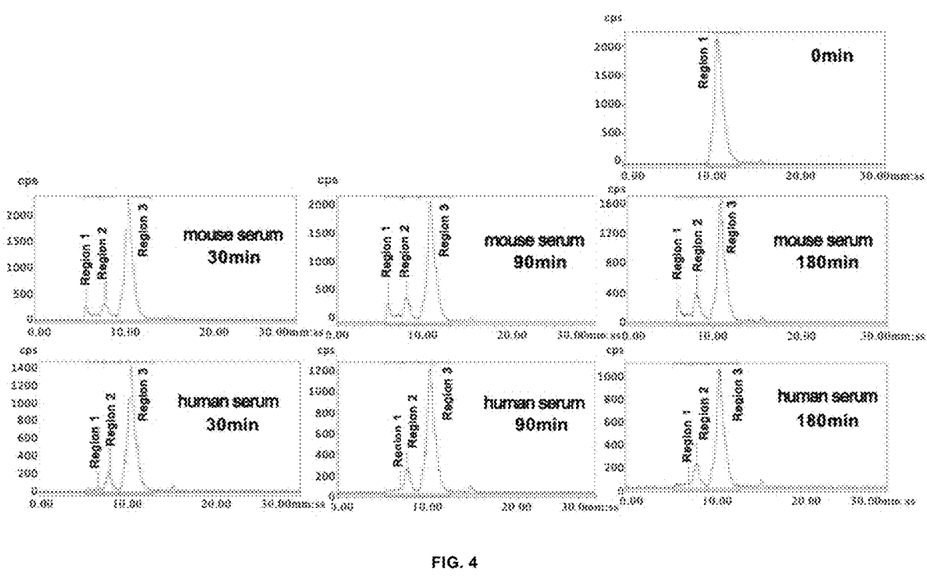
FIG. 4 shows the HPLC spectrum of the anti-PD-L1 nanobody. The contents and compositions were examined for stability at different time points after incubation of anti-PD-L1 nanobodies with mouse and human serums, respectively.

(6) 5×10$^5$ of HCC827 cells with high PD-L1 expression or 5×10$^5$ of A549 cells with low PD-L1 expression were inoculated in the right armpit of nude mice and the tumor was grown to the size of 150-200 mm$^3$ for the study (7) Tumor-bearing mice were anesthetized with isoflurane and were injected through tail vein either with Tc-99m labeled nanobodies (~10 ug, 5 MBq) or labeled nanobodies mixed with 20× unlabeled nanobodies, or were injected through tail vein with Atezolizumab 72 hours ago. Scanning was performed 0.5 hr after the administration, and the data was collected with static 15 min SPECT and medium resolution whole body CT The results are shown in FIG. 4. The HPLC spectrum showed that that nanobody No. 2 was incubated in vitro up to 180 minutes without any degradation and was very stable.

The HPLC results of nanobody No. 1 and nanobody No. 3, which were not specifically shown in the figure, were similar to that of nanobody No. 2

Figure 5:
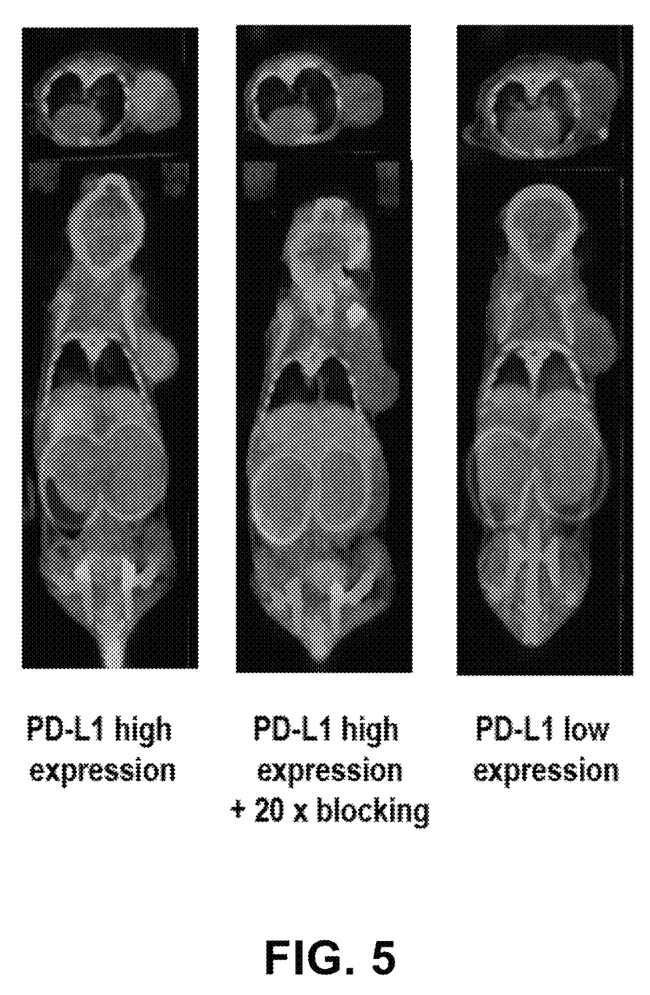
FIG. 5 shows the SPECT-CT imaging result of the 99mTc labeled PD-L1 nanobody in tumor-bearing mice with high PD-L1 expression. Nanobodies can effectively accumulate in tumors with high PD-L1 expression, and non-binding antibodies can be quickly cleared from the blood through kidney and bladder.

FIG. 5 and Table 3 show the 30 minute SPECT scan pictures and the bio-distribution data of tumor-bearing mice. The results showed that nanobody No. 2 can effectively accumulate in the tumor with high PD-L1 expression for the non-invasive detection of PD-L1 expression and can be used for the prognosis and diagnosis of cancer. The imaging results of nanobody of No. 1 and nanobody No. 3, which were not specifically shown in the figure, were similar to that of nanobody No. 2.

TABLE 3

In vivo distribution of 99m-Tc labeled anti-PD-L1 nanobodies in tumor-bearing mice

| Name Organ | PD-L1 high expression | PD-L1 high expression + 20 x blocking | PD-L1 low expression |
|---|---|---|---|
| Heart | 1.03 ± 0.27 | 0.49 ± 0.02 | 0.48 ± 0.01 |
| Lung | 1.53 ± 0.39 | 1.35 ± 0.15 | 0.70 ± 0.16 |
| Liver | 1.92 ± 0.10 | 0.77 ± 0.11 | 1.70 ± 0.06 |
| Kidney | 53.08 ± 5.94 | 25.59 ± 2.91 | 41.22 ± 1.60 |
| Bladder | 109.58 ± 48.47 | 239.21 ± 97.48 | 84.36 ± 12.86 |
| Muscle | 0.41 ± 0.18 | 0.15 ± 0.03 | 0.20 ± 0.08 |
| Tumor | 1.27 ± 0.14 | 0.54 ± 0.20 | 0.19 ± 0.03 |
| Tumor/Heart | 1.62 ± 0.48 | 1.08 + 0.38 | 0.40 ± 0.07 |
| Tumor/Muscle | 5.97 ± 2.67 | 3.70 + 1.48 | 1.07 ± 0.26 |

All literatures mentioned in the present invention are cited as a reference in this application, just like each literature is separately cited as a reference. In addition, it should be understood that person skilled in the art may make various changes or modifications to the invention after reading the above information of the invention. These equivalent formats also fall within the scope of the claims attached in the application.

The invention claimed is:

1. An immunoconjugate, comprising:
   (a) a VHH chain of an anti-PD-L1 nanobody wherein the amino acid sequence of the VHH chain is any one of SEQ ID NOs: 1-3; and
   (b) a conjugating moiety selected from the group consisting of a detectable label, a drug, a toxin, a cytokine, a radionuclide, an enzyme antibody, an antibody Fc fragment, an antibody scFv fragment, a gold nanoparticle, a gold nanorod, a virus particle, a liposome, a magnetic nanoparticle, and a cell.

2. The immunoconjugate of claim 1, wherein the radionuclide is either:
   (i) a diagnostic radioisotope, which is selected from the group consisting of Tc-99m, Ga-68, F-18, I-123, I-125, In-111, Ga-67, Cu-64, Zr-89, C-11, and combinations thereof; or
   (ii) a therapeutics radioisotope, which is selected from the group consisting of Lu-177, Y-90, Ac-225, As-211, Bi-212, Bi-213, Cs-137, Cr-51, Co-60, Dy-165, Er-169, Fm-255, Au-198, Ho-166, I-125, I-131, Ir-192, Fe-59, Pb-212, Mo-99, Pd-103, P-32, K-42, Re-186, Re-188, Sm-153, Ra223, Ru-106, Na24, Sr89, Tb-149, Th-227, Xe-133, Yb-169, Yb-177, and combinations thereof.

3. The immunoconjugate of claim 1, wherein the drug is a cytotoxic drug.

4. The immunoconjugate of claim 1, wherein the toxin is selected from the group consisting of an auristatin, chlortetracycline, methanesol, ricin, A-chain of ricin, cobustine, dokamicin, dorastatin, adriamycin, daunorubicin, paclitaxel, cisplatin, cc1065, ethidium bromide, mitomycin, etoposide, tenoposide, vincristine, vinblastine, colchicine, dihydroxyanthrax diketone, actinomycin, diphtheria toxin, Pseudomonas exotoxin (PE) A, PE40, acacia bean toxin, acacia bean toxin A chain, capsule root toxin A chain, a-sarcissus, gelonin, mitogellin, retstrictocin, phenolmycin, Eenomycin, curicin, croton toxin, calicheamicin, Sapaonaria officinalis inhibitor, glucocorticoid, and combinations thereof.

5. A PD-L1 detection agent, which comprises the immunoconjugate of claim 1 and a pharmaceutically acceptable detection aid.

6. The PD-L1 detection agent of claim 5, wherein the detection aid is selected from the group consisting of an isotope tracer, a contrast agent, a FACS detection reagent, an immunofluorescence detection reagent, a magnetic nanoparticle, and an imaging agent.

7. A pharmaceutical composition, which comprises the immunoconjugate of claim 1 and a pharmaceutically acceptable carrier.

8. A detection kit for PD-L1 expression, which comprises the immunoconjugate of claim 1 and an instruction manual.

9. A VHH chain of an anti-PD-L1 nanobody, wherein the amino acid sequence of the VHH chain is any one of SEQ ID NOs:1-3.

10. A method of treating a disease, comprising administering the immunoconjugate of claim 1 to a subject in need thereof, wherein the disease is a PD-L1 positive tumor or cancer, and wherein the PD-L1 positive tumor or cancer is selected from the group consisting of gastric cancer, lymphoma, liver cancer, leukemia, kidney tumor, lung cancer, small intestine cancer, bone cancer, prostate cancer, colorectal cancer, breast cancer, large intestine cancer, prostate cancer, adrenal tumor, and any combinations thereof.

11. A method of treating a disease, comprising administering the pharmaceutical composition of claim 7 to a subject in need thereof, wherein the disease is a PD-L1 positive tumor or cancer, and wherein the PD-L1 positive tumor or cancer is selected from the group consisting of gastric cancer, lymphoma, liver cancer, leukemia, kidney tumor, lung cancer, small intestine cancer, bone cancer, prostate cancer, colorectal cancer, breast cancer, large intestine cancer, prostate cancer, adrenal tumor, and any combinations thereof.

12. The immunoconjugate of claim 3, wherein the cytotoxic drug is selected from the group consisting of an antitubulin drug, a DNA groove binding agent, a DNA replication inhibitor, an alkylation agent, an antibiotic, a folic acid antagonist, an antimetabolite, a chemotherapy sensitizer, a topoisomerase inhibitor, a vinca alkaloid, and any combinations thereof.

13. The immunoconjugate of claim 4, wherein the auristatin is selected from the group consisting of auristatin E, auristatin F, monomethylolastatin-E (MMAE), monomethylolastatin-D (MMAD), and monomethylolastatin-F (MMAF).

14. The pharmaceutical composition of claim 7, wherein the pharmaceutically acceptable carrier is a non-toxic and inert aqueous carrier.

15. The pharmaceutical composition of claim 7, wherein the pharmaceutically acceptable carrier is selected from a group consisting of a physiological saline, a phosphate buffer solution, dextrose, glycerol, ethanol, water, and an aqueous solution containing glucose.

16. The pharmaceutical composition of claim 7, wherein the composition is an injectable composition.

17. The method of treatment according to claim 11, wherein the pharmaceutical composition is administered through an intratumoral route, an intraperitoneal route, an intravenous route, or a topical route.

* * * * *